United States Patent [19]

Onsager et al.

[11] 4,209,650
[45] Jun. 24, 1980

[54] PROCESS FOR PRODUCING ETHYLENE GLYCOL

[75] Inventors: Olav T. Onsager, Suffern, N.Y.; Peter L. Szecsi, Montclair, N.J.

[73] Assignee: Halcon International, Inc., New York, N.Y.

[21] Appl. No.: 691,112

[22] Filed: May 28, 1976

[51] Int. Cl.² ............................................. C07C 29/02
[52] U.S. Cl. .................................................. 568/860
[58] Field of Search ........................... 260/636, 635 H; 568/860

[56] References Cited

U.S. PATENT DOCUMENTS

| | | | |
|---|---|---|---|
| 1,982,545 | 11/1934 | Skarblom | 260/636 |
| 2,071,395 | 2/1937 | Dreyfus | 260/635 H |
| 3,360,548 | 12/1967 | Clark et al. | 260/635 H |
| 4,061,868 | 12/1977 | Fumagalli et al. | 568/860 |

FOREIGN PATENT DOCUMENTS 45-36291  11/1970  Japan .................................. 260/635 H Primary Examiner—Joseph E. Evans
Attorney, Agent, or Firm—William C. Long; David Dick; Riggs T. Stewart

[57] ABSTRACT

Ethylene glycol is prepared by the reaction of ethylene, molecular oxygen and water in the presence of an iodine catalyst and in the presence of a copper co-catalyst or promoter.

3 Claims, No Drawings

PROCESS FOR PRODUCING ETHYLENE GLYCOL

This invention relates to the preparation of ethylene glycol, and is more particularly concerned with a process for directly producing ethylene glycol by the molecular oxygen oxidation of ethylene in the presence of water and in the presence of iodine or an iodine-liberating compound as a catalyst.

Ethylene glycol is a chemical of acknowledged commercial importance and it is used, for example, in the preparation of anti-freeze compositions and in the manufacture of polyester fibers. Various processes for the manufacture of ethylene glycol have been proposed, including those based upon the hydrolysis of ethylene oxide or the hydrolysis of carboxylate esters of ethylene glycol. U.S. Pat. No. 1,982,545, in the name of Skärblom, discusses the liquid-phase preparation of ethylene glycol directly from ethylene by reacting the ethylene with molecular oxygen in the presence of iodine or of a substance capable of readily liberating iodine under the conditions of the reaction. The overall reaction may be represented as follows:

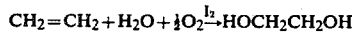

$$CH_2=CH_2+H_2O+\tfrac{1}{2}O_2 \xrightarrow{I_2} HOCH_2CH_2OH$$

In the Skarblom process, the reaction takes place in a plurality of reaction chambers into which water and a mixture of ethylene and oxygen are introduced under superatmospheric pressure. More recently, Witheford, U.S. Pat. No. 3,928,474 disclosed a variation of the Skärblom process involving the handling of the liquid reaction product in a particular way.

While ethylene glycol is indeed produced in the processes described in these prior disclosures, there is a continuing desire to increase the rate of reaction in order to reduce the reaction times required to produce meaningful quantities of ethylene glycol.

It is accordingly an object of the present invention to provide a process for producing ethylene glycol from ethylene, molecular oxygen and water at a greater rate than has heretofore been possible in processes using iodine or iodine-liberating compounds as catalysts.

It is a further object of the invention to provide a process of the character indicated by means of which substantial quantities of ethylene glycol can be effectively produced in relatively short periods of time.

Other objects and features of the invention will be readily apparent from the following detailed description of illustrative embodiments thereof.

In accordance with the invention, ethylene, water and molecular oxygen are reacted in the liquid phase in the presence of iodine or of an iodine-liberating compound and in the presence of a copper compound used in relatively small amounts and serving as a co-catalyst or promoter. The quantity of copper compound used in accordance with the invention may vary from 10 ppm to 5 wt %, based upon liquid reaction mixture. Preferably, the amount of copper compound is 20 ppm to 2 wt. % and most preferably 50 ppm to 1 wt. %.

The copper compound which may be used as a co-catalyst or promoter in accordance with the process of the invention may be any cuprous or cupric compound which is at least partially soluble in the reaction mixture, e.g., has a solubility of at least about 10 ppm in the reaction mixture. Illustrative of typical copper compounds of this character are the copper salts of mineral acids, such as copper sulfate, copper phosphate, copper iodide, copper bromide, and copper chloride, copper oxides such as $Cu_2O$ and $CuO$, copper salts of organic acids such as copper carbonate, copper acetate, copper butyrate, copper oleate and like carboxylic acids, preferably containing up to 20 carbon atoms. Particularly preferred are cuprous iodide, cuprous oxide and cupric oxide. It is to be understood that the compounds referred to above are given for illustrative purposes only and that other copper compounds having the desired solubility can be used, as will be readily apparent to persons skilled in the art.

The iodine-liberating compound can be any compound capable of producing iodide ions in solution under the oxidation conditions. For example, the iodine-liberating compound can be an inorganic compound such as HI, or a metal iodide, such as $FeI_2$, $FeI_3$, $CrI_2$, $ZnI_2$, and like iodine compounds which hydrolyze to form HI, or it can be an organic iodine compound. In particular, the organic iodine compounds include all the iodine derivatives of the ethylene oxidized and of the reaction products. For example, in the oxidation of ethylene these include but are not limited to 1,2 diiodoethane, iodohydrin and other iodine containing derivatives of ethylene and including iodine derivatives of higher molecular weight ethers, and the like. Indeed, since many organic iodine compounds are formed in the course of the reaction and these iodine moieties can be recycled to the oxidation zone, if desired, the net supply of iodine to the system is at a minimum. In general, the quantity of iodine, expressed as HI, is in the range of about 0.1 to 20 wt. % of the liquid reaction mixture.

The oxidation zone into which the ethylene, molecular oxygen, water, iodine or iodine-liberating compound, and the copper co-catalyst are charged is kept under a superatmospheric pressure sufficient to maintain the liquid phase. Ordinarily, a pressure in the range of 10 to 2000 psig, preferably 20 to 1000 psig, is employed although higher or lower pressures may be used depending on the temperature, as long as the liquid phase is maintained. Temperatures of the order of 50° to 250° C. are generally suitable for the reaction, but preferably the temperature is in the range of 75° to 200° C., and most preferably a temperature of 100° to 180° C. is employed.

Generally, substantially stoichiometric quantities of ethylene, oxygen, and water are employed along with a catalytically-effective quantity of iodine or of an iodine-liberating compound and a small but effective amount of the copper co-catalyst promoter, but other ratios of ethylene, oxyygen and water can be employed. For example, the molar ratio of ethylene to oxygen can vary from 100:1 to 1:100 and the ratio of ethylene to water can vary from 10:1 to 1:100.

While the invention is applicable to batch reaction in which all of the reactants and all of the components are initially charged to the oxidation zone and the reaction is carried out without further additions until the desired extent of the reaction has been achieved, preferably the reaction is carried out concintuously and the copper co-catalyst lends itself readily to continuous operation in which it can be continuously recycled to the oxidation zone along with the iodine moieties. The copper co-catalyst of the invention can be used in the systems described in the above-mentioned Skärblom and Witheford patents, but there is disclosed in the application of Olav T. Onsager and Peter Szecsi entitled "Preparation of Ethylene Glycol" (Case 1097), being filed concurrently herewith a continuous process which is particularly adapted for use with the catalyst system of this invention and accordingly the disclosure of said application is incorporated herein by reference. That copending application describes the separation of the liquid reaction mixture which is removed from the reaction zone into a plurality of portions or fractions, including a higher-boiling residual portion which will include sufficient higher-boiling organic compounds to keep this fraction in a fluid condition, and may also include some of the iodine moieties in the form of organic iodine compounds, and the recycling of that residual fraction to the reaction zone. The copper co-catalyst or promoter will be present in this heavy fraction and will thus be recycled so that the need for adding additional quantities of copper compounds will be minimized.

It will be understood, however, that the use of the copper co-catalyst or promoter of this invention with the iodine or iodine-liberating catalyst previously discussed is not limited to any particular batch or continuous operation and the beneficial effects of using this catalyst combination are realized in whatever reaction system it may be employed.

The advantages and features of the invention will be more fully understood from the following examples of typical operation of the processes of the invention. It will be understood, however, that these examples are being given for illustrative purposes only.

EXAMPLE 1

A 1-liter titanium autoclave was charged with 500 g. of an aqueous solution containing 8.3 g. hydrogen iodide and pressured to 360 psig with ethylene. The autoclave was heated to 160° C. and ethylene and oxygen were admitted at a rate to keep the percentage of oxygen in the off gas between 7 and 9%. After 4 hours, the autoclave was cooled down and discharged. Analysis of the effluent gave the following composition: ethylene glycol 3.9 wt. %, 2-iodoethanol 0.26 wt. % and p-dioxane 0.08 wt. % for a total net make of 0.34 mole of glycol moieties. By-product acetaldehyde represented 0.038 mole and $CO_2$ amounted to 0.01 mole.

EXAMPLE 2

A 1-liter titanium autoclave was charged with 500 g. of an aqueous solution containing 8.3 g. hydrogen iodide and 0.19 g. cuprous iodide. The reaction was conducted for 4 hours under the same conditions as described in Example 1. Analysis of the effluent gave the following composition: ethylene glycol 10 wt. %, 2-iodoethanol 0.66 wt. %, diethylene glycol 1.08 wt. %, monoiododiethylene glycol 0.19 wt. % and p-dioxane 0.55 wt. % for a total net make of 1.128 moles of glycol moieties. By-product acetaldehyde represented 0.069 mole and $CO_2$ amounted to 0.03 mole.

What is claimed is:

1. In a process for the preparation of ethylene glycol by the reaction of reactants consisting essentially of ethylene, molecular oxygen and water in the presence of an iodine catalyst at a temperature of 50° to 250° C. and under a pressure sufficient to maintain the liquid phase, the improvement which comprises the addition of a copper co-catalyst or promoter to the reaction system, the copper co-catalyst being present in the amount of 10 ppm to 5 wt. percent based upon the liquid reaction mixture and the iodine catalyst, expressed as HI, being present in the amount of 0.1 to 20 wt. percent of the liquid reaction mixture, the molar ratio of ethylene to oxygen varying from 100:1 to 1:100 and the ratio of ethylene to water varying from 10:1 to 1:100.

2. A process as defined in claim 1, wherein the copper co-catalyst or promoter is employed in the form of cuprous iodide, cuprous oxide and cupric oxide.

3. A process as defined in claim 1, wherein substantially stoichiometric quantities of ethylene, oxygen and water are employed.

* * * * *